United States Patent [19]

Kaper

[11] Patent Number: 4,885,181

[45] Date of Patent: Dec. 5, 1989

[54] PROCESS FOR DECAFFEINATING GREEN COFFEE

[75] Inventor: Louris Kaper, Barneveld, Netherlands

[73] Assignee: Douwe Egberts Koninklijke Tabaksfabriek-Koffiebranderijen-Theehandel, N.V., Utrecht, Netherlands

[21] Appl. No.: 300,722

[22] Filed: Jan. 25, 1989

Related U.S. Application Data

[63] Continuation of Ser. No. 55,879, Jun. 1, 1987, abandoned.

[30] Foreign Application Priority Data

| May 30, 1986 | [NL] | Netherlands | 8601400 |
| May 30, 1986 | [NL] | Netherlands | 8601401 |
| Jul. 8, 1986 | [NL] | Netherlands | 8601783 |
| Aug. 6, 1986 | [NL] | Netherlands | 8602011 |

[51] Int. Cl.$^4$ .............................................. A23F 5/22
[52] U.S. Cl. ................................ 426/422; 426/427; 544/274
[58] Field of Search ............... 544/274, 275; 426/422, 426/427

[56] References Cited

U.S. PATENT DOCUMENTS

| 4,298,736 | 11/1981 | Katz et al. ............................ 544/274 |
| 4,481,223 | 11/1984 | Hinman et al. ................... 544/274 X |
| 4,513,136 | 4/1985 | Katz et al. ....................... 544/274 X |
| 4,540,784 | 9/1985 | Vitzthum et al. ................... 544/274 |
| 4,548,827 | 10/1985 | Katz et al. ............................. 426/427 |

FOREIGN PATENT DOCUMENTS

| 1123656 | 5/1982 | Canada ............................... 426/427 |
| 0008398 | 3/1980 | European Pat. Off. . |
| 0042295 | 12/1981 | European Pat. Off. . |
| 8204803 | 12/1981 | European Pat. Off. . |
| 0076620 | 4/1983 | European Pat. Off. . |
| 0111375 | 6/1984 | European Pat. Off. . |
| 0129609 | 1/1985 | European Pat. Off. . |

*Primary Examiner*—Joseph Golian
*Attorney, Agent, or Firm*—Cushman, Darby & Cushman

[57] ABSTRACT

A process for decaffeinating green coffee by extraction of the coffee with water and treatment of the aqueous extract with activated carbon whereby the caffeine is largely absorbed by the activated carbon. The resulting caffeine-loaded activated carbon is then treated with a selected acid whereby the caffeine is largely removed from the activated carbon. The carbon is then washed with water until it has pH in the range of 3 to 6, determined by the standard test method for pH of activated carbon (ASTM D 3838-80). The activated carbon is then ready to be reused more than ten times in the process without further treatment.

5 Claims, No Drawings

PROCESS FOR DECAFFEINATING GREEN COFFEE

This is a continuation of application Ser. No. 055,879, filed June 1, 1987, which was abandoned upon the filing hereof.

The present invention relates to a process for decaffeinating green coffee by extraction of the coffee with water and treatment of the aqueous extract with activated carbon.

In addition to the processes for decaffeinating green coffee using chlorinated hydrocarbons, which have been commercially practiced in the past, processes for decaffeinating green coffee using activated carbon have received increasing attention. In such a process there an extract of green coffee is first prepared said extract containing the directly water-soluble dry substance, in addition to caffeine. This prepared extract is then treated with activated carbon, which adsorbs caffeine to the carbon.

According to European patent application 111375, this process is carried out using an activated carbon having a specific caffeine adsorptivity of at least 100 g of caffeine per kg of carbon, a specific selectivity of at least 0.2, said carbon showing a positive correlation between the concentration of bean extract, on the one hand, and the loading ratio of caffeine/non-caffeine-extracted substances in the adsorbent, on the other hand, when this is in equilibrium with the bean extract.

According to European patent application 8398, the activated carbon is preloaded with sugar, if required, in combination with a treatment with acid, prior to removing the caffeine from the extract. The use of such a process prevents too much non-caffeine dry substance from being removed from the extract. A drawback of this process is that the reuse of the activated carbon requires that it to be thermally regenerated and reactivated.

European patent application 40712 relates to the decaffeination of green coffee beans in the manner described above in the opening paragraph, using a "substantially neutral active carbon." In the application this process is further defined as an activated carbon of substantially neutral reaction when dispersed in water. One of the drawbacks of this process is that the attendant decomposition of the chlorogenically acid components in the extract may cause a noticeable deviation in flavor.

As regards the recovery of the caffeine from the activated carbon loaded therewith, various processes are known which substantially result in the specific choice of the solvent. European patent application 42295 relates to inter alia, the use of acetic acid or mixtures thereof with other components for the recovery of the caffeine from the activated carbon. A drawback of this process, as elucidated in European patent application 76620, is that acetic acid has a very low flashpoint, so that this process is essentially not commercially acceptable. The said European patent application therefore relates to a process for reducing this problem, which is achieved by abandoning a part of the positive effects of the acetic acid by diluting it with at least 30% water. As a result thereof, the flashpoint is considerably raised, but this is at the expense of extraction efficiency. However, also according to these processes, the activated carbon should be thermally regenerated or reactivated after recovery of the caffeine.

European patent application 129609 relates to the use of formic acid and/or formic acid-containing solutions for the recovery of caffeine. Although this process has a fairly reasonable efficiency, it is still necessary to thermally regenerate the activated carbon in the course of time.

The object of the present invention is to provide a process for decaffeinating green coffee using carbon, which is commercially marketable and does not require thermal regeneration of the carbon after caffeine recovery.

An aqueous green coffee extract is treated with an activated carbon. The caffeine-loaded activated carbon is then treated with selected acid whereby the caffeine is largely removed from the activated carbon. The carbon is then washed with water until it has a pH in the range of 3 to 6, determined by the Standard Test Method for pH of Activated Carbon (ASTMD 3838-80). The activated carbon is ready to be reused in the process without further treatment.

Surprisingly, it has been found that the combination of specific steps according to the invention leads to an efficient decaffeination process which further has some advantages over the prior art. One of the advantages is that intermediate thermal regeneration of the carbon can be dispensed with, or that this regeneration is necessary only very occasionally.

A second advantage is that the process claimed gives no problems with the formation of substances that give rise to a deviation in flavor of the treated coffee after roasting, which is probably due to the fact that a reduced decomposition of the chlorogenic acids occurs.

The extraction to be used according to the invention takes place in the usual manner by treatment of the green coffee with water or with an aqueous solution at a temperature ranging from 50° to 100° C.

The carbon used in the process according to the invention may be a commercially sold carbon. This carbon should be selected according to the property of having, after acid regeneration and washing with water, a pH ranging from 3 to 6, preferably from 3 to 5.5, as determined by the Standard Test Method for pH of Activated Carbon (ASTMD 3838-80).

For a first selection an activated carbon may be chosen, which, in itself, satisfies the pH requirement. This is not yet sufficient per se, because it should also be verified that the carbon can be brought to a pH of 3 to 6 by aqueous washing after acid treatment to remove caffeine.

It is well-known that activated carbon comprises oxygen-containing groups which, depending on the nature and structure, are of an either acidic or basic character. For use in the present invention it is important that the basic groups in the activated carbon are optimally shielded.

In this connection it is observed that the activated carbon described in European patent application 40712 must have, by definition, both acid and basic groups, because a neutral reaction means that the acid and basic groups mutually balance. Such a carbon is less suitable according to the invention, because it acts more adversely with respect to catalytizing by-product formation.

As is obvious from the examples of European patent application 40712, the use of the carbon described therein leads to an increase in the pH of the extract, which means that the basic groups are not or only partly shielded. From a viewpoint of flavor this is very disadvantageous.

The process according to the invention, however, does not lead or hardly leads to a change of the pH of the extract, which has clear advantages.

The activated carbon to be used according to the invention preferably has a large internal surface area, said internal surface area preferably being more than 800 m² per g (BET), since with carbons having such an internal surface area the amount of adsorbed caffeine can be brought into proper ratio with respect to the amount of other adsorbed dry substance.

After loading with the caffeine, which may occur in the conventional manner, e.g., as described in European patent applications 8398, 40712, 111375, or 140629, the caffeine-loaded carbon is treated with an acid liquid. This treatment preferably takes place at a temperature of least 100° C., more preferably above 110° C., under atmospheric pressure, the selection of the acid liquid being such that the evaporation at the above temperature is rather limited. In practice this means that, in principle, this process is carried out at best at the boiling point of the acid liquid under atmospheric pressure.

The acid liquid may consist either of the acid as such, of a mixture of two or more acids, or of a combination of acid or a mixture of acids with one or more other substances. Specific examples of acid liquids to be used are glacial acetic acid, acetic acid diluted with water, lactic acid, glycolic acid, citric acid, phosphoric acid, benzoic acid, or combinations of two or more of these acids, optionally with water. Preferably, however, use is made of an acid liquid containing 50–85 wt.%, preferably at least 65 wt.% acetic acid, while the remaining liquid may consist of water, citric acid, phosphoric acid, lactic acid, benzoic acid, and the like.

After treatment with the acid liquid the activated carbon is completely or nearly completely liberated from the caffeine. This caffeine is then contained in the acid liquid, from which it can be removed by using well-known techniques.

The carbon liberated from caffeine is then washed with water, until the carbon satisfies the requirements imposed with respect to its pH. This carbon is then used again for adsorbing caffeine from the aqueous coffee extract. Of course, it is also possible to wash the carbon with a diluted aqueous solution of the acid, used in the decaffeination process.

The activated carbon is preferably used without preloading. However, it is possible to treat the carbon before use in the decaffeination step with a carbohydrate solution. Pretreatment with ethyl cellulose, as described in European Patent Application is preferably not done.

After adjustment of a condition of balance, the above-described process leads to a caffeine adsorption to the carbon corresponding to 80-95% of the original adsorptivity.

Such a process permits to arrive at a residual caffeine content of the coffee of not more than 0.1 wt.%. When this value increases, the initial level can be restored by readjustment of the coffee/carbon ratio.

The example that follows is intended to illustrate the invention. It is not intended to limit the invention beyond its claims.

EXAMPLE

Green coffee having a caffeine content of 1.2 wt.% was extracted with water for 6 hours at a temperature of 70° C.

This extraction was effected by alternately passing the liquid over the coffee to be extracted and over a carbon column. The extract was thus treated with activated carbon, and then there was obtained an extract having a pH of 4.8, substantially liberated from caffeine.

After the experiment was finished, the wet green coffee was dried and combined with the extract. The caffeine content of the finally obtained green coffee was 0.1 wt.% (based on the green coffee). The activated carbon originated from an earlier cycle, followed by regeneration in the manner described hereinafter The caffeine-loaded activated carbon (23.4 g caffeine/kg activated carbon) was desorbed at 112° C. with acetic acid (100%). Then there was obtained a nearly complete desorption of the caffeine. The carbon thus liberated from caffeine was then washed with water again, until the carbon had a pH of 5.2 and was ready to be reused in the next cycle.

The above-described process relates to the stable situation in which more than 10 of such cycles had already taken place.

I claim:

1. A process for decaffeinating aqueous green coffee extract which comprises:
   (a) treating said extract with activated carbon recycled from step (d) wherein the caffeine is largely absorbed by the activated carbon to form caffeine-loaded activated carbon;
   (b) treating said caffeine-loaded activated carbon with an acid, or a mixture of one or more acids selected from the group consisting of acetic acid, citric acid, lactic acid, phosphoric acid, and benzoic acid whereby the caffeine is largely removed from the said caffeine-loaded carbon;
   (c) washing the said activated carbon with water until it has a pH ranging from 3 to 5.5;
   (d) recycling the activated carbon to step (a) whereby the steps (a) through (d) are repeated more than ten times without thermal regeneration.

2. A process according to claim 1, comprising treating the carbon with the acid solution which is liquid at atmospheric pressure at the treatment temperature which is at least 100° C. and preferably 110° C.

3. A process according to claim 1, wherein the carbon has a surface of at least 800 m²/g (BET).

4. A process for decaffeinating aqueous green coffee extract which consists of:
   (a) treating said extract with activated carbon recycled from step (d) wherein the caffeine is largely absorbed by the activated carbon to form caffeine-loaded activated carbon;
   (b) treating said caffeine-loaded activated carbon with an acid, or a mixture of one or more acids selected from the group consisting of acetic acid, citric acid, lactic acid, phosphoric acid, and benzoic acid whereby the caffeine is largely removed from the said caffeine-loaded carbon;
   (c) washing the said activated carbon with water until it has a pH ranging from 3 to 5.5;
   (d) recycling the activated carbon to step (a) whereby the steps (a) through (d) are repeated more than ten times without thermal regeneration.

5. A process for decaffeinating green coffee wherein green coffee is extracted to give an aqueous green coffee extract comprising decaffeinating the said aqueous green coffee extract using the process of claim 1 and combining the said obtained green coffee extract with the said extracted green coffee.

* * * * *